(12) United States Patent
Okuno

(10) Patent No.: US 12,295,757 B2
(45) Date of Patent: May 13, 2025

(54) MEDICAL IMAGE PROCESSING DEVICE, METHOD, AND PROGRAMS THAT CUT OUT REGION FROM SECOND MEDICAL IMAGE TO GENERATE SECOND PARTIAL IMAGE FOR SUPERIMPOSE ON FIRST MEDICAL IMAGE, AND MEDICAL IMAGE DISPLAY SYSTEM

(71) Applicant: FUJIFILM Corporation, Tokyo (JP)

(72) Inventor: Takuma Okuno, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 332 days.

(21) Appl. No.: 17/898,414

(22) Filed: Aug. 29, 2022

(65) Prior Publication Data

US 2022/0409147 A1 Dec. 29, 2022

Related U.S. Application Data

(63) Continuation of application No. PCT/JP2021/007302, filed on Feb. 26, 2021.

(30) Foreign Application Priority Data

Mar. 5, 2020 (JP) ................. 2020-037840

(51) Int. Cl.
 *A61B 6/03* (2006.01)
 *G06T 7/70* (2017.01)
 *A61B 5/055* (2006.01)

(52) U.S. Cl.
 CPC ............... *A61B 6/03* (2013.01); *G06T 7/70* (2017.01); *A61B 5/055* (2013.01); *G06T 2207/10088* (2013.01)

(58) Field of Classification Search
 None
 See application file for complete search history.

(56) References Cited

U.S. PATENT DOCUMENTS 8,953,865 B2 * 2/2015 Goto .................... A61B 5/4514
 382/132
9,514,384 B2 12/2016 Ishihara et al.
(Continued)

FOREIGN PATENT DOCUMENTS

JP 2000287955 10/2000
JP 2006167169 6/2006
(Continued)

OTHER PUBLICATIONS

"International Search Report (Form PCT/ISA/210) of PCT/JP2021/007302," mailed on May 18, 2021, with English translation thereof, pp. 1-7.

(Continued)

*Primary Examiner* — Haris Sabah
(74) *Attorney, Agent, or Firm* — JCIPRNET

(57) ABSTRACT

Provided are a medical image processing device, a medical image processing method, a program, and a medical image display system that reduce the amount of movement of a line of sight in a case in which a medical image is observed. A first medical image of a subject is displayed. A second medical image including an anatomical feature structure closest to a designated position in the first medical image is acquired. The first medical image and the second medical image are registered. A region including the identified anatomical feature structure is cut out from the second medical image based on a registration result to generate a second partial region image. The second partial region image is displayed to be superimposed on the first medical image.

17 Claims, 6 Drawing Sheets

(56) References Cited

U.S. PATENT DOCUMENTS

| | | | |
|---|---|---|---|
| 2008/0226145 A1 | 9/2008 | Moriya | |
| 2008/0253631 A1 | 10/2008 | Oosawa | |
| 2011/0228994 A1 | 9/2011 | Tanaka et al. | |
| 2012/0004556 A1* | 1/2012 | Rold | A61B 8/12 600/463 |
| 2014/0016845 A1 | 1/2014 | Gazit et al. | |
| 2018/0024995 A1 | 1/2018 | Choi et al. | |
| 2019/0164639 A1* | 5/2019 | Saaraswat | G06F 16/2365 |
| 2020/0243184 A1* | 7/2020 | Nagata | G06T 15/06 |

FOREIGN PATENT DOCUMENTS

| | | |
|---|---|---|
| JP | 2008212396 | 9/2008 |
| JP | 2008259622 | 10/2008 |
| JP | 2008289548 | 12/2008 |
| JP | 2015208539 | 11/2015 |
| JP | 2017051591 | 3/2017 |
| WO | 2005009242 | 2/2005 |
| WO | 2010047324 | 4/2010 |

OTHER PUBLICATIONS

"Written Opinion of the International Searching Authority (Form PCT/ISA/237)" of PCT/JP2021/007302, mailed on May 18, 2021, with English translation thereof, pp. 1-6.
"Office Action of Japan Counterpart Application", issued on Aug. 10, 2023, with English translation thereof, p. 1-p. 7.

* cited by examiner

MEDICAL IMAGE PROCESSING DEVICE, METHOD, AND PROGRAMS THAT CUT OUT REGION FROM SECOND MEDICAL IMAGE TO GENERATE SECOND PARTIAL IMAGE FOR SUPERIMPOSE ON FIRST MEDICAL IMAGE, AND MEDICAL IMAGE DISPLAY SYSTEM

CROSS-REFERENCE TO RELATED APPLICATIONS

The present application is a Continuation of PCT International Application No. PCT/JP2021/007302 filed on Feb. 26, 2021 claiming priority under 35 U.S.C § 119(a) to Japanese Patent Application No. 2020-037840 filed on Mar. 5, 2020. Each of the above applications is hereby expressly incorporated by reference, in its entirety, into the present application.

BACKGROUND OF THE INVENTION

1. Field of the Invention

The present invention relates to a medical image processing device, a medical image processing method, a program, and a medical image display system and particularly relates to a technique for displaying a plurality of medical images.

2. Description of the Related Art

In the medical field, a change over time in a region of interest between a medical image captured in the past and a current medical image is observed.

JP2015-208539A discloses an image display device that displays computed tomography (CT) images captured at different times in parallel.

SUMMARY OF THE INVENTION

In a case in which the current image and the past image are arranged side by side on a viewer as in the device disclosed in JP2015-208539A, a distance between the current image and the past image on the viewer is long. Therefore, the amount of movement of the line of sight of a user is large, and there is a problem in that the load of a visual recognition operation is large.

The invention has been made in view of the above circumstances, and an object of the invention is to provide a medical image processing device, a medical image processing method, a program, and a medical image display system that reduce the amount of movement of a line of sight in a case in which a medical image is observed.

In order to achieve the above object, according to an aspect of the invention, there is provided a medical image processing device comprising: a memory that stores commands to be executed by a processor; and the processor that executes the commands stored in the memory. The processor outputs a signal for displaying a first medical image of a subject, acquires a position, which is designated by a user, in the first medical image, identifies an anatomical feature structure closest to the designated position in the first medical image, acquires a second medical image of the subject that was captured in the past and that includes the identified anatomical feature structure, registers the first medical image with the second medical image, cuts out a region including the identified anatomical feature structure from the second medical image based on a registration result to generate a second partial region image, and outputs a signal for displaying the second partial region image to be superimposed on the first medical image.

According to this aspect, the region including the identified anatomical feature structure is cut out from the second medical image to generate the second partial region image, and the signal for displaying the second partial region image to be superimposed on the first medical image is output. Therefore, it is possible to reduce the amount of movement of the line of sight in a case in which the medical image is observed.

Preferably, the processor estimates a position of the identified anatomical feature structure in the second medical image and registers the first medical image with the second medical image, using a position of the identified anatomical feature structure in the first medical image and the estimated position of the anatomical feature structure in the second medical image. This makes it possible to register the anatomical feature structures without any deviation even in a case in which there are a body movement and a respiratory movement in the capture of a medical image.

Preferably, the processor cuts out a region including the identified anatomical feature structure from the first medical image to generate a first partial region image and outputs a signal for displaying the first partial region image side by side with the second partial region image. This makes it possible to reduce the amount of movement of the line of sight in a case in which the first partial region image and the second partial region image are observed.

Preferably, the processor outputs a signal for displaying a frame, which surrounds a region including the identified anatomical feature structure of the first medical image, to be superimposed on the first medical image. This enables the user to recognize the region of the first medical image corresponding to the second partial region image.

Preferably, the processor outputs a signal for displaying a difference image indicating a difference between the first medical image and the second medical image to be superimposed on the first medical image. This enables the user to recognize the difference between the first medical image and the second medical image.

Preferably, the processor adjusts a quality of the first medical image under a first image quality adjustment condition and adjusts a quality of the second medical image under the first image quality adjustment condition. Since the quality of the first medical image and the quality of the second medical image are adjusted under the same image quality adjustment conditions, it is easy to observe the first medical image and the second partial region image.

Preferably, the anatomical feature structure includes at least one of an organ, a bone, a muscle, or a lesion region. This aspect is suitable for observing the organs, the bones, the muscles, and the lesion regions.

Preferably, the first medical image and the second medical image include an image captured by any of a computed tomography (CT) device, a magnetic resonance imaging (MRI) device, a positron emission tomography (PET) device, an ultrasound diagnostic device, or a computed radiography (CR) device. This aspect is suitable for observation using the medical images captured by the CT device, the Mill device, the PET device, the ultrasound diagnostic device, and the CR device.

In order to achieve the above object, according to another aspect of the invention, there is provided a medical image display system comprising: the above-described medical image processing device; a display that displays an image based on an acquired signal; and an input device that designates a position in the image displayed on the display.

According to this aspect, the region including the anatomical feature structure which is closest to the position of the first medical image designated by the input device is cut out from the second medical image to generate the second partial region image, and the second partial region image is displayed on the display so as to be superimposed on the first medical image. Therefore, it is possible to reduce the amount of movement of the line of sight in a case in which the medical image is observed.

In order to achieve the above object, according to still another aspect of the invention, there is provided a medical image processing method comprising: a first medical image display step of outputting a signal for displaying a first medical image of a subject; a designated position acquisition step of acquiring a position, which is designated by a user, in the first medical image; an anatomical feature structure identification step of identifying an anatomical feature structure closest to the designated position in the first medical image; a second medical image acquisition step of acquiring a second medical image of the subject that was captured in the past and that includes the identified anatomical feature structure; a registration step of registering the first medical image with the second medical image; a second medical image cutout step of cutting out a region including the identified anatomical feature structure from the second medical image based on a registration result to generate a second partial region image; and a second medical image display step of outputting a signal for displaying the second partial region image to be superimposed on the first medical image.

According to this aspect, the region including the identified anatomical feature structure is cut out from the second medical image to generate the second partial region image, and the signal for displaying the second partial region image to be superimposed on the first medical image is output. Therefore, it is possible to reduce the amount of movement of the line of sight in a case in which the medical image is observed.

This aspect also includes a program that causes a computer to execute each step of the above-described medical image processing method and a non-transitory computer-readable recording medium on which the program is recorded.

According to the invention, it is possible to reduce the amount of movement of the line of sight in a case in which medical images are observed.

DESCRIPTION OF THE PREFERRED EMBODIMENTS

Hereinafter, a preferred embodiment of the invention will be described in detail with reference to the accompanying drawings.

<Display of Image According to Related Art>

Figure 1:
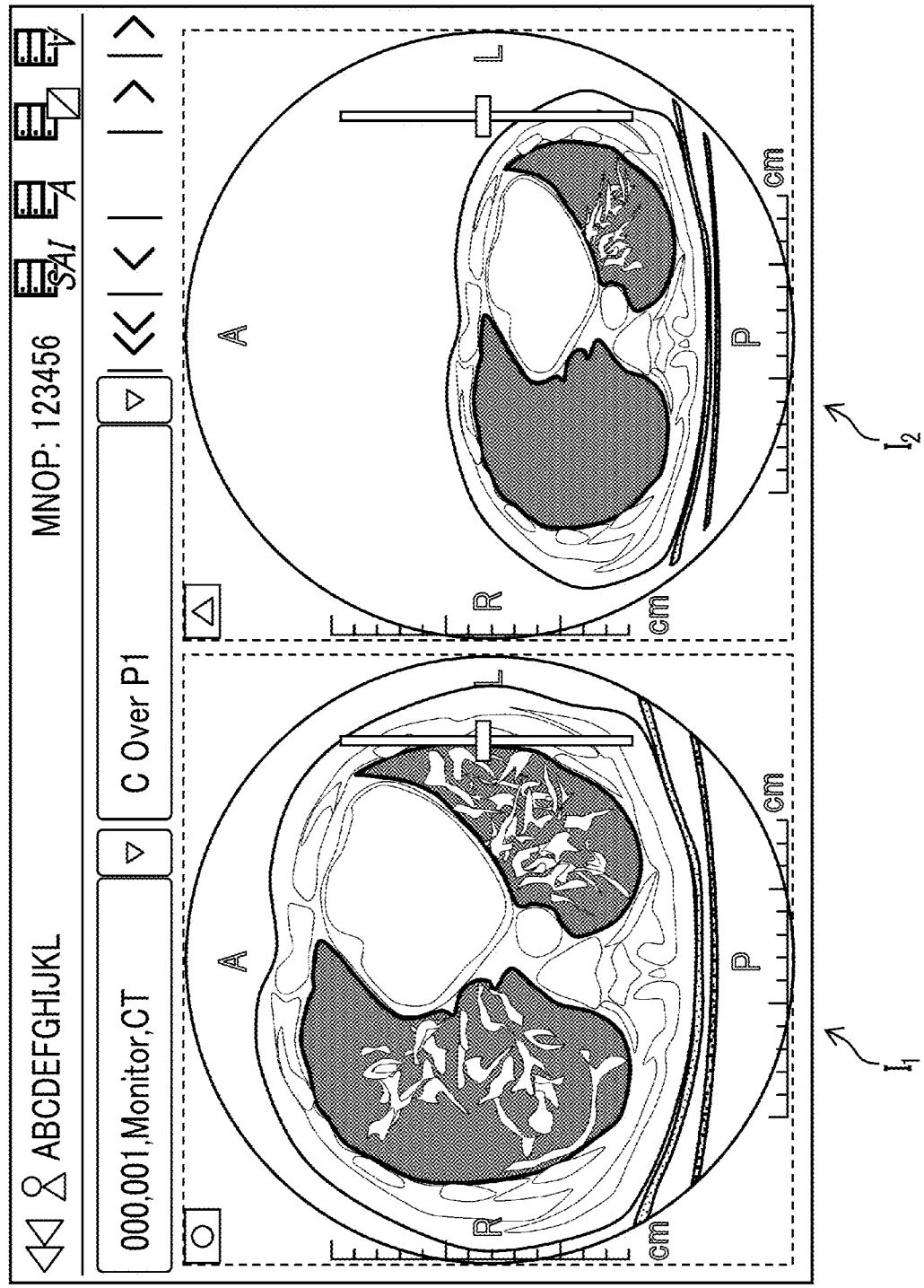
FIG. 1 is a diagram illustrating an example of comparison display of medical images according to the related art.

FIG. 1 is a diagram illustrating an example of comparison display of medical images according to the related art. In the example illustrated in FIG. 1, a current image $I_1$ which is a current medical image of a subject and a past image $I_2$ of the same subject which corresponds to the current image $I_1$ are displayed side by side.

A user, such as a doctor, can compare the current image $I_1$ with the past image $I_2$ displayed as illustrated in FIG. 1 to observe the progress of a region of interest such as an anatomical feature structure.

However, in a case in which the current image and the past image are displayed as illustrated in FIG. 1, there is a problem in that the amount of movement of a line of sight of the user in the observation of the region of interest is large.

<Configuration of Medical Image Display System>

Figure 2:
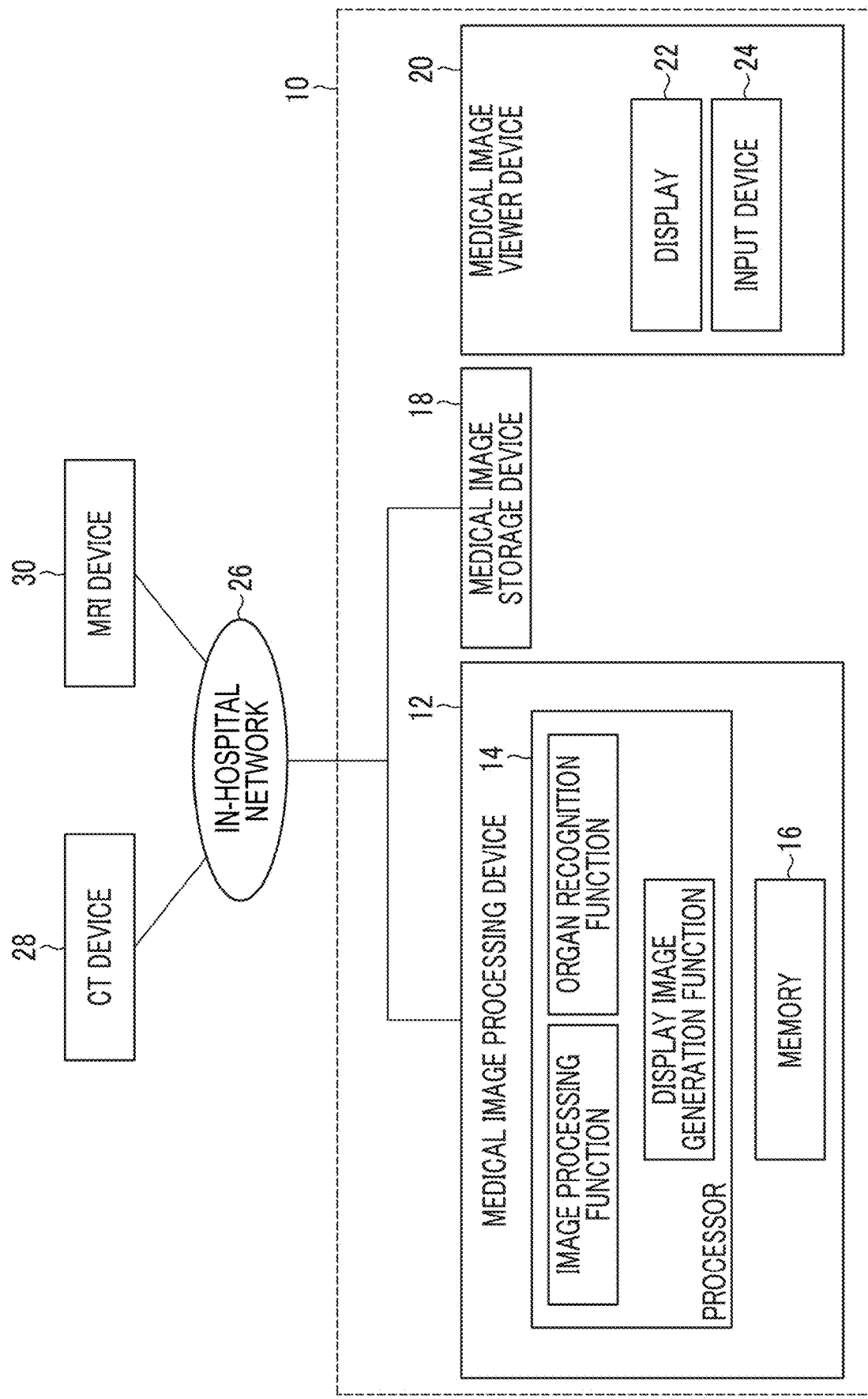
FIG. 2 is a block diagram illustrating a medical image display system according to this embodiment.

The configuration of a medical image display system according to this embodiment will be described. FIG. 2 is a block diagram illustrating a medical image display system 10. As illustrated in FIG. 2, the medical image display system 10 comprises a medical image processing device 12, a medical image storage device 18, and a medical image viewer device 20.

The medical image processing device 12 is, for example, a computer that is used in a hospital. The medical image processing device 12 comprises a processor 14 and a memory 16.

The memory 16 stores commands to be executed by the processor 14. In the medical image processing device 12, the processor 14 executes a program including the commands read from the memory 16 to implement various functions including an image processing function, an organ recognition function, and a display image generation function.

The medical image storage device 18 includes a large-capacity storage that stores medical images. The medical image storage device 18 stores the medical images to which accessory information defined by a Digital Imaging and Communication in Medicine (DICOM) standard has been added.

The medical image viewer device 20 is a device used by the user to observe the medical images. The medical image viewer device 20 includes a display 22 and an input device 24.

The display 22 is a display device that displays an image based on a signal acquired from the medical image processing device 12. The medical image stored in the medical image storage device 18 is displayed on the display 22.

The input device 24 is a device used by the user to designate a desired position on the image displayed on the display 22. The input device 24 comprises, for example, a mouse (not illustrated) for moving a pointer and performing a click operation.

The medical image display system 10 is connected to an in-hospital network 26.

The in-hospital network 26 is implemented by, for example, a local area network (LAN). The medical image display system 10 is connected to a computed tomography (CT) device 28 and a magnetic resonance imaging (MRI) device 30 through the in-hospital network 26. For example, a positron emission tomography (PET) device, an ultrasound diagnostic device, or a computed radiography (CR) device may be connected to the in-hospital network 26.

<Method for Storing Extracted Region Data of Anatomical Feature Structure>

Figure 3:
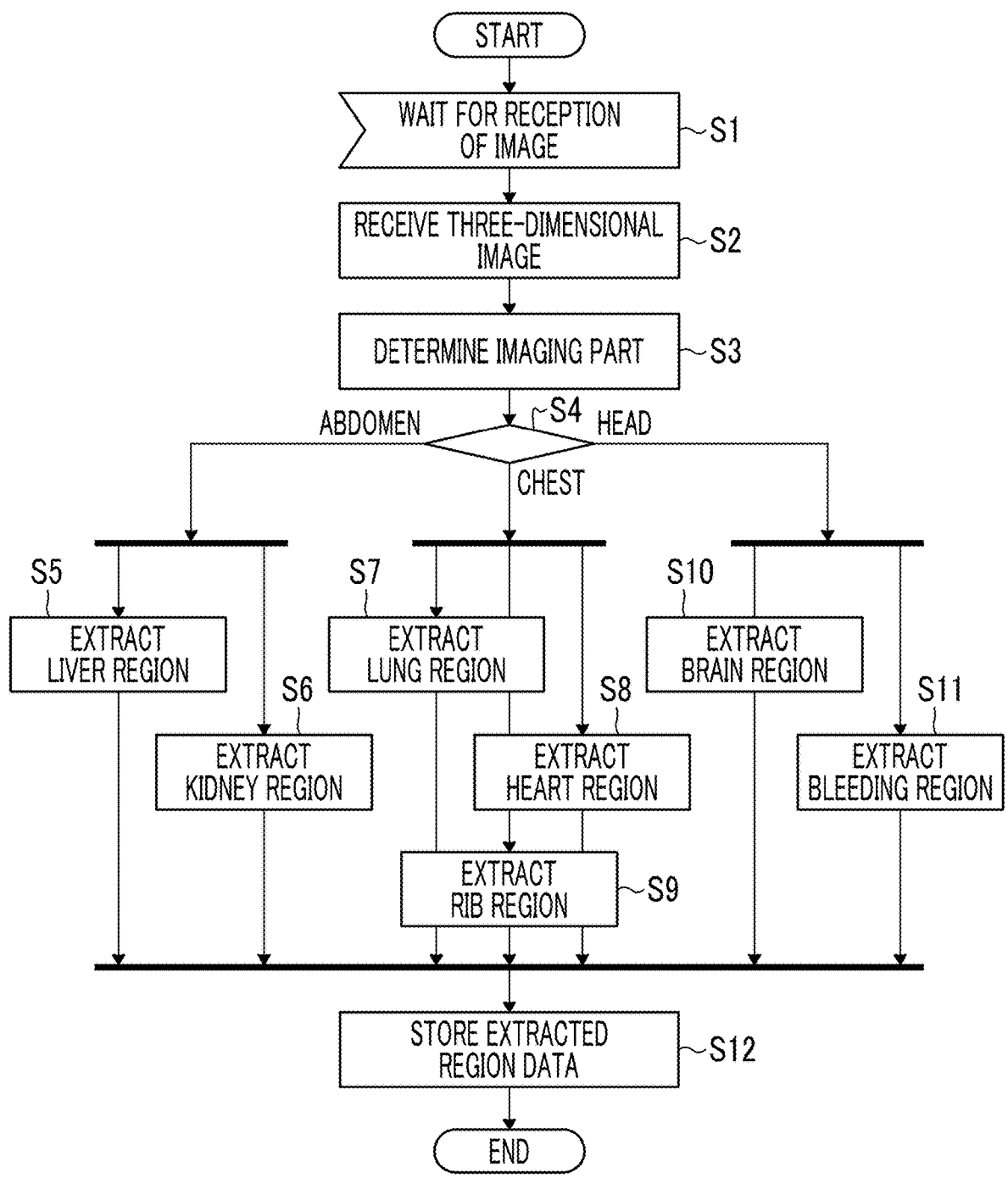
FIG. 3 is a flowchart illustrating a process of a method for storing extracted region data of an anatomical feature structure in a medical image.

FIG. 3 is a flowchart illustrating a process of a method for storing extracted region data of an anatomical feature structure in the medical image.

The anatomical feature structures are parts and regions that become landmarks in a body such as organs, bones, muscles, and lesion regions. The organs include a brain, a heart, a lung, a stomach, intestines, pancreas, a right kidney, a left kidney, a spleen, a liver, and the like. The bones include a spine. The spine includes cervical vertebrae, thoracic vertebrae, and lumbar vertebrae. The muscles include erector spinae muscles, lateral muscles, rectus abdominis muscles, psoas major muscles, quadratus lumborum muscles, and the like. The lesion region includes a bleeding region and a tumor region.

There is a case in which any anatomical feature structure requires follow-up observation. Therefore, all of the anatomical feature structures are follow-up observation objects. In addition, the medical image processing device 12 may extract at least one of the anatomical feature structures.

In Step S1, the medical image processing device 12 is in a state in which it waits for the reception of the medical image.

In a case in which the CT device 28 captures a three-dimensional CT image, the captured three-dimensional CT image is transmitted to the medical image processing device 12 through the in-hospital network 26. Similarly, in a case in which the MRI device 30 captures a three-dimensional MRI image, the captured three-dimensional MRI image is transmitted to the medical image processing device 12 through the in-hospital network 26.

In Step S2, the medical image processing device 12 receives the three-dimensional images transmitted from the CT device 28 and the MM device 30 as the medical images.

In Step S3, the medical image processing device 12 determines an imaging part of the received medical image. The medical image processing device 12 determines the imaging part using a known image recognition process such as pattern matching. The medical image processing device 12 may determine the imaging part using a trained machine learning model.

In Step S4, the medical image processing device 12 is allocated to an anatomical feature structure extraction process corresponding to the imaging part determined in Step S3.

In a case in which the imaging part determined in Step S3 is an abdomen, the medical image processing device 12 extracts a liver region from the medical image in Step S5 and extracts a kidney region from the medical image in Step S6.

In a case in which the imaging part determined in Step S3 is a chest, the medical image processing device 12 extracts a lung region from the medical image in Step S7, extracts a heart region from the medical image in Step S8, and extracts a rib region from the medical image in Step S9.

In a case in which the imaging part determined in Step S3 is a head, the medical image processing device 12 extracts a brain region from the medical image in Step S10 and extracts a bleeding region from the medical image in Step S11.

The medical image processing device 12 performs the process of extracting each anatomical feature structure using the trained machine learning model. After ending the process of extracting the anatomical feature structures, the medical image processing device 12 performs a process in Step S12.

In Step S12, the medical image processing device 12 stores the extracted region data of the extracted region in the medical image storage device 18 for each type of the extracted region so as to be associated with the medical image.

In this way, the medical image processing device 12 ends the process of the method for storing the extracted region data of the anatomical feature structures.

<Medical Image Display Method>

A medical image display method according to this embodiment will be described. In addition, in this embodiment, the current image is, for example, a medical image having the latest imaging date and time among the medical images obtained by imaging the subject and is not limited to the current image displayed at the present time. Further, the past image is, for example, a medical image obtained by imaging the same subject as the current image and is a medical image having an earlier imaging date and time than the current image. In this embodiment, a first medical image and a second medical image captured at different times may be displayed. In addition, a past image and an older past image may be displayed.

Figure 4:
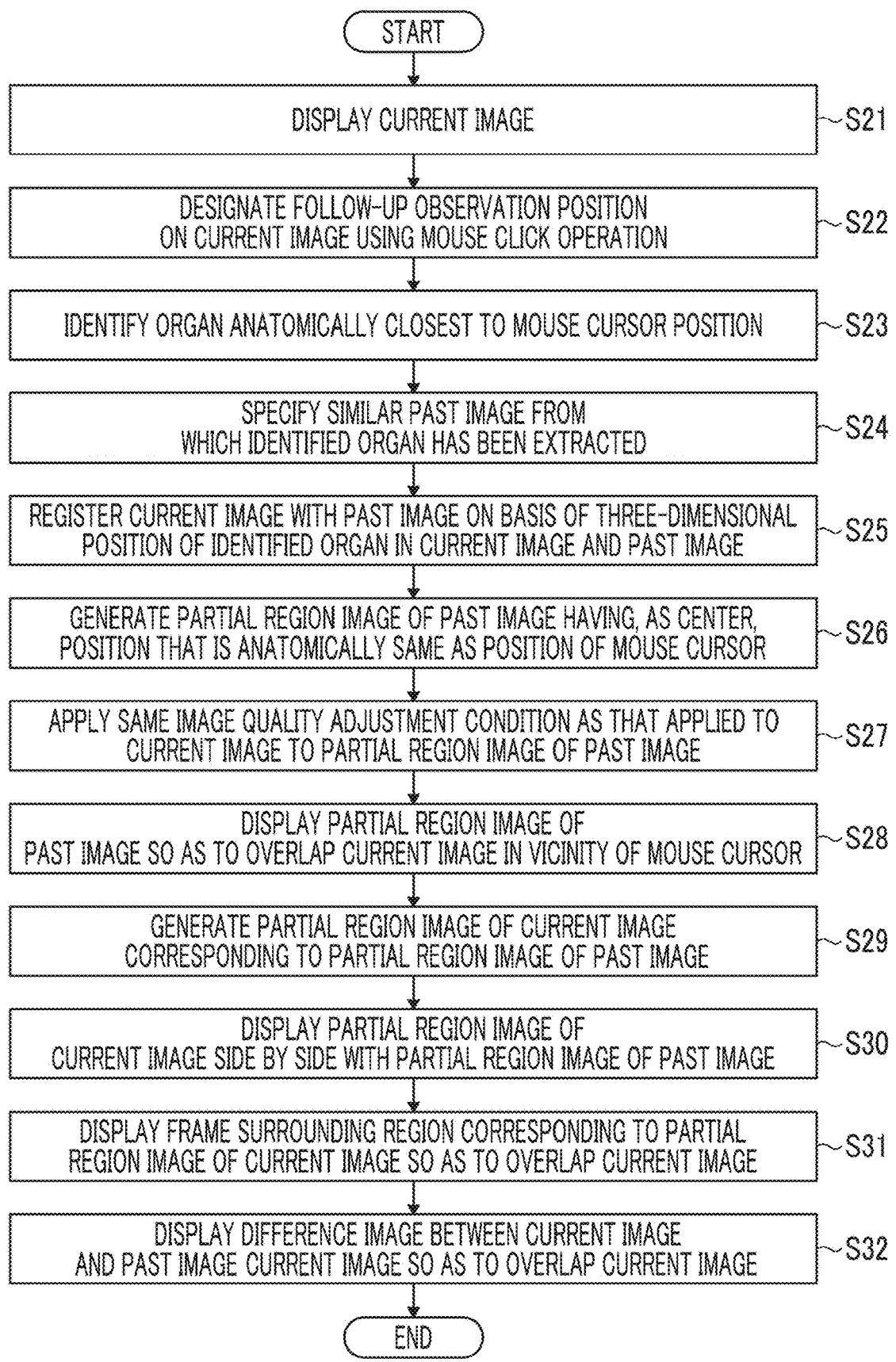
FIG. 4 is a flowchart illustrating a process of a medical image display method.

FIG. 4 is a flowchart illustrating a process of the medical image display method.

First, in Step S21 (an example of a first medical image display step), the user designates the current image of the subject using the input device 24 of the medical image viewer device 20. The medical image processing device 12 reads the designated current image from the medical image storage device 18 and outputs a signal for displaying the designated current image to the medical image viewer device 20, in response to an input from the input device 24. The medical image viewer device 20 acquires the signal and displays the designated current image on the display 22 on the basis of the acquired signal.

In Step S22 (an example of a designated position acquisition step), the user designates a position in the current image displayed on the display 22 using the input device 24 of the medical image viewer device 20. Here, the user uses the mouse to move a mouse cursor to a desired position and performs a mouse click and drag operation to designate a position of interest to be subjected to follow-up observation in the current image. The medical image processing device 12 acquires the designated position of interest in the current image.

In Step S23 (anatomical feature structure identification step), the medical image processing device 12 identifies an organ (an example of the anatomical feature structure) that is anatomically closest to the position of interest designated in the current image in Step S22.

As described with reference to FIG. 3, the medical image stored in the medical image storage device 18 is associated in advance with the extracted region data of the anatomical feature structures including the organ. Therefore, the medical image processing device 12 can identify the organ that is anatomically closest to the designated position of interest, using the extracted region data. In addition, in a case in which there are a plurality of organs that are anatomically closest to the designated position of interest, an organ having a predetermined high priority may be selected.

In Step S24 (an example of a second medical image acquisition step), the medical image processing device 12 specifies a past image, which includes the same subject as the current image displayed on the display 22 and is similar to the current image, and acquires the past image from the medical image storage device 18. Here, a past image including the organ identified in Step S23 is specified. The medical image processing device 12 can acquire the past image including the organ identified in Step S23, using the extracted region data of the anatomical feature structure associated with the medical image.

In Step S25 (an example of a registration step), the medical image processing device 12 registers the current image with the past image on the basis of the three-dimensional position of the organ identified in Step S23. Here, the medical image processing device 12 estimates the position of the organ identified in Step S23 in the current image and the position of the organ identified in Step S23 in the past image. Further, the medical image processing device 12 performs registration using the position of the organ in the current image and the position of the organ in the past image.

In a case in which the organ identified in Step S23 is a non-rigid organ, such as the liver and the lung, it is preferable to perform non-rigid registration between the current image and the past image to improve the position accuracy of the past image to be cut out. A known method can be used as the non-rigid registration.

In a case in which the size of the current image is different from the size of the past image, the past image may be resized to the size of the current image, and then the registration may be performed.

In Step S26 (an example of a second medical image cutout step), the medical image processing device 12 cuts out a region including the anatomical feature structure identified in Step S23 from the past image on the basis of the result of the registration in Step S25 to generate a past partial region image (an example of a second partial region image). Here, the medical image processing device 12 cuts out a region of interest, which has, as the center, a position that is anatomically the same as the position of interest designated in Step S22 in the current image, from the past image to generate the past partial region image.

In Step S27, the medical image processing device 12 applies a first image quality adjustment condition which is an image quality adjustment condition applied to the current image to adjust the quality of the past partial region image. An image quality adjustment process may include, for example, a gradation conversion process that converts the gradation of a brightness value of an input image into a different gradation and a sharpness process that enhances an edge.

In addition, the medical image processing device 12 may apply the first image quality adjustment condition to adjust the quality of the past image and then generate the past partial region image.

Further, in a case in which the image quality adjustment process is not performed on the current image, the medical image processing device 12 may adjust the quality of the current image under the first image quality adjustment condition and adjust the quality of the past partial region image under the same first image quality adjustment condition.

In Step S28 (an example of a second medical image display step), the medical image processing device 12 outputs a signal for displaying the past partial region image generated in Step S26 so as to overlap the current image. The medical image viewer device 20 acquires the signal and displays the image on the display 22. Then, the past partial region image is displayed on the display 22 of the medical image viewer device 20 so as to be superimposed on the current image. It is preferable that the past partial region image is displayed so as to be superimposed on the current image at a position which does not cover the region of interest that is anatomically the same as that in the past partial region image generated in Step S26. The position where the past partial region image is placed may be designated with the mouse.

In Step S29, the medical image processing device 12 cuts out a region including the anatomical feature structure identified in Step S23 from the current image to generate a current partial region image (an example of a first partial region image). Here, the medical image processing device 12 cuts out the region of interest that is anatomically the same as that in the past partial region image generated in Step S26.

In Step S30, the medical image processing device 12 overlaps the current partial region image generated in Step S29 with the current image and outputs a signal for displaying the current partial region image side by side with the past partial region image. The medical image viewer device 20 acquires the signal and displays the image on the display 22. Then, the past partial region image and the current partial region image are displayed side by side on the display 22 of the medical image viewer device 20 so as to be superimposed on the current image. It is preferable that the current partial region image is displayed at a position that does not cover the region of interest of the current image, similarly to the past partial region image.

In Step S31, the medical image processing device 12 outputs a signal for displaying a frame that surrounds the region of interest corresponding to the current partial region image generated in Step S29 in the current image displayed on the display 22 so as to overlap the current image. The medical image viewer device 20 acquires the signal and displays the image on the display 22. Therefore, a frame indicating the range of the current partial region image is displayed on the display 22 of the medical image viewer device 20 so as to be superimposed on the current image.

In Step S32, the medical image processing device 12 generates a difference image between the current image displayed on the display 22 and the past image acquired in Step S24 and outputs a signal for displaying the generated difference image so as to overlap the current image. The medical image viewer device 20 acquires the signal and displays the image on the display 22. Therefore, the difference image is displayed on the display 22 of the medical image viewer device 20 so as to be superimposed on the current image.

The difference image may be, for example, an image obtained by changing at least one of brightness, saturation, or hue of the current image for a difference region.

Then, the medical image processing device 12 ends the process of the medical image display method. In addition, the above-described process can be repeatedly performed in response to a mouse drag operation to perform comparison display with the past image while seamlessly moving the region of interest at the same time.

Figure 5:
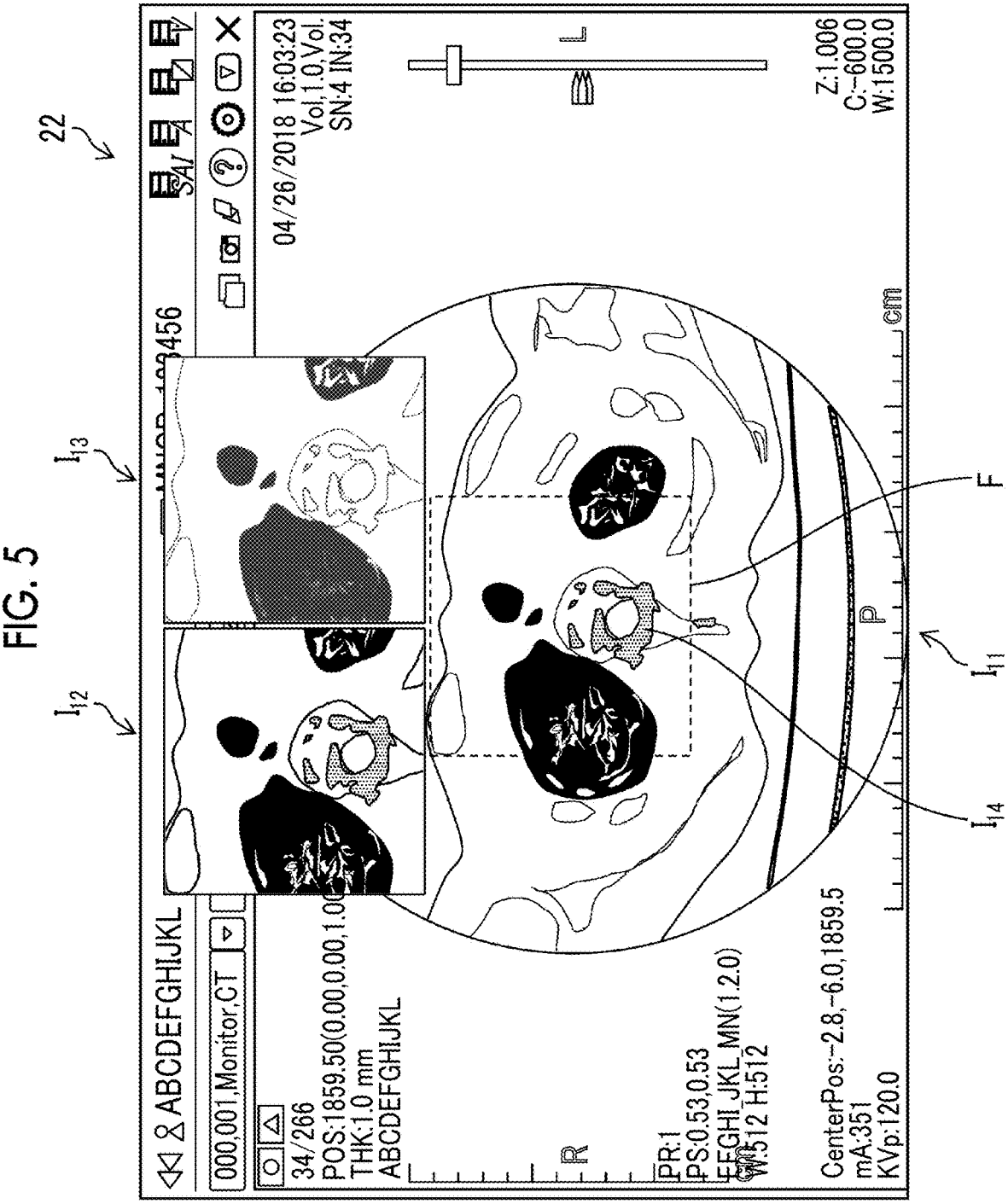
FIG. 5 is a diagram illustrating an example of the comparison display of the medical images according to this embodiment.

FIG. 5 is a diagram illustrating an example of the comparison display of the medical images according to this embodiment. As illustrated in FIG. 5, a current image $I_{11}$, a current partial region image $I_{12}$ generated from the current image $I_{11}$, a past partial region image $I_{13}$ generated from a past image corresponding to the current image $I_{11}$, a difference image $I_{14}$ between the current image $I_{11}$ and the corresponding past image, and a frame F surrounding the region of interest of the current image $I_{11}$ are displayed on the display 22 of the medical image viewer device 20. Here, the frame F is configured by a broken line. However, the color and line type of the frame F may be appropriately selected.

The current image $I_{11}$ is displayed at the center of the display 22. The current partial region image $I_{12}$ and the past partial region image $I_{13}$ are displayed side by side so as to be superimposed on the current image $I_{11}$. In addition, the current partial region image $I_{12}$ and the past partial region image $I_{13}$ are displayed at positions that do not overlap the frame F.

Further, the difference image $I_{14}$ is displayed so as to be superimposed on the current image $I_{11}$. The difference image $I_{14}$ is a difference image of a bone region between the current image $I_{11}$ and the corresponding past image. That is, in the example illustrated in FIG. 5, bone difference display is performed.

In the bone difference display illustrated in FIG. 5, since the overlay display of the difference image $I_{14}$ on the current image $I_{11}$ is performed, it is preferable to display not only the past partial region image $I_{13}$ but also the current partial region image $I_{12}$ excluding the overlay display. In the example illustrated in FIG. 5, three images of the same region of interest are displayed simultaneously and adjacent to each other. Therefore, the amount of movement of the line of sight during observation is reduced.

Here, all of the current image, the current partial region image, the past partial region image, the difference image, and the frame are displayed. However, only necessary information may be displayed as appropriate.

In a case in which there are a plurality of past images, the past images may be displayed side by side. In addition, in a case in which there are a plurality of past images, the past images may be switched by at least one of a mouse wheel operation, a right-click operation, or a key operation to smoothly perform follow-up observation in a predetermined display region regardless of the number of past images.

It is considered that the vicinity of the same tumor in the past image is cut out and displayed so as to overlap the current image in a case in which tumor registration has been performed by the examination from the past to the present (tumor tracking) and any tumor has been designated in the current image.

Figure 6:
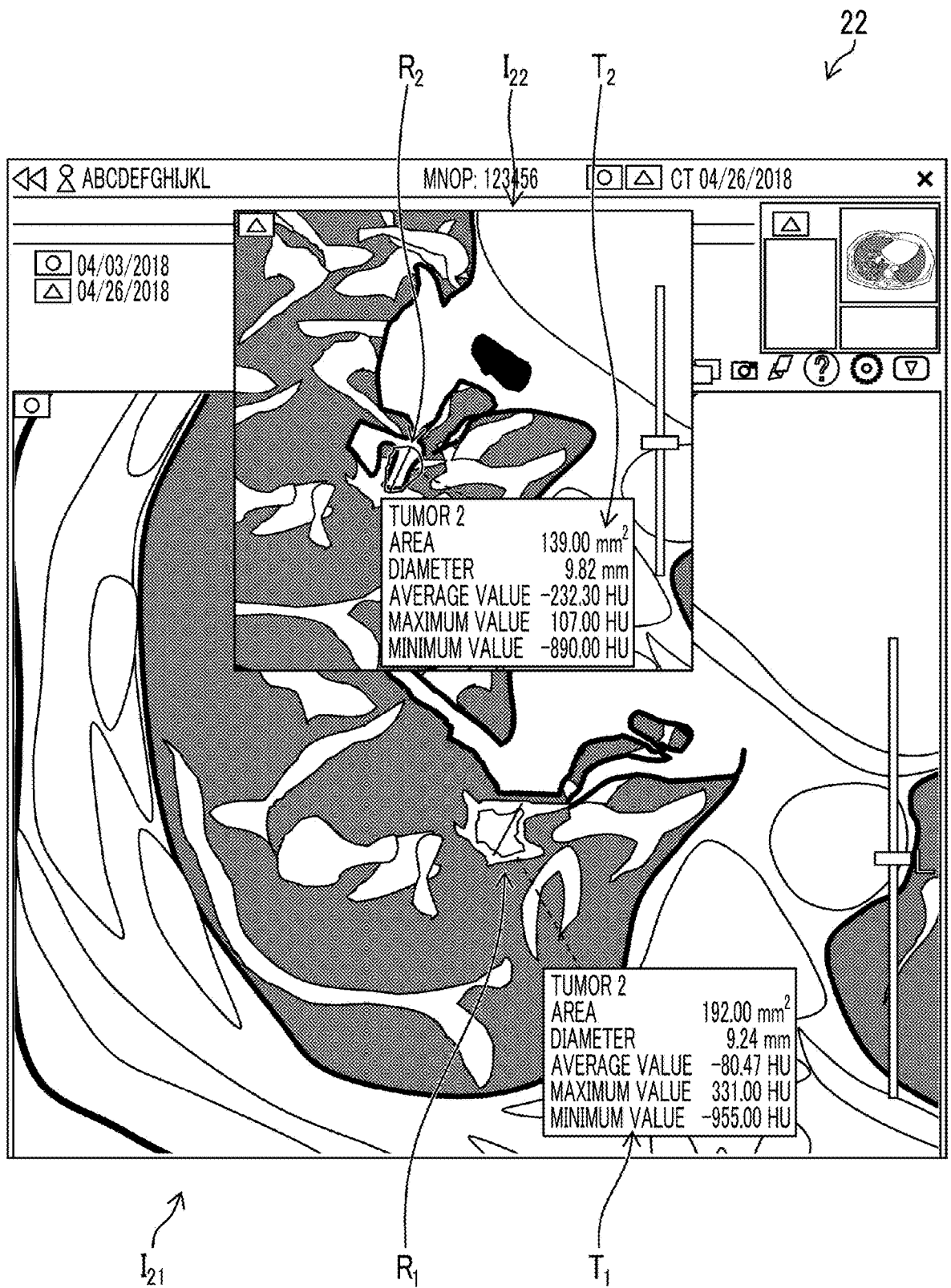
FIG. 6 is a diagram illustrating an example of the comparison display of the medical images in a case in which a tumor is designated.

FIG. 6 is a diagram illustrating an example of the comparison display of the medical images in a case in which a tumor is designated. As illustrated in FIG. 6, a current image $I_{21}$ is displayed on the display 22 of the medical image viewer device 20. The current image $I_{21}$ includes a tumor region $R_1$.

In a case in which the tumor region $R_1$ is designated as the position of interest from the current image $I_{21}$, the medical image processing device 12 acquires a past image including a tumor region corresponding to the designated tumor region $R_1$ from the medical image storage device 18. Further, the medical image processing device 12 performs the registration between the current image $I_{21}$ and the past image and then generates a past partial region image $I_{22}$ from the past image. Furthermore, the medical image processing device 12 outputs a signal for displaying the past partial region image $I_{22}$ so as to be superimposed on the current image $I_{21}$.

As a result, as illustrated in FIG. 6, the past partial region image $I_{22}$ is displayed on the display 22 so as to be superimposed on the current image $I_{21}$. The past partial region image 122 includes a tumor region $R_2$ corresponding to the tumor region.

This display of the medical images makes it possible to reduce the amount of movement of the line of sight in a case in which the user observes the tumor region.

In addition, in the example illustrated in FIG. 6, information $T_1$ of the tumor region $R_1$ is displayed so as to be superimposed on the current image $I_{21}$. Similarly, information $T_2$ of the tumor region $R_2$ is displayed so as to be superimposed on the past partial region image $I_{22}$. The information $T_1$ and the information $T_2$ include the areas, major axes, average values, maximum values, and minimum values of the tumors $R_1$ and $R_2$, respectively. The information is stored in the medical image storage device 18 so as to be associated with the medical image. This display of the information of the tumor makes it possible to appropriately perform the follow-up observation of the tumor.

<Other>

In this embodiment, the mouse is used as the input device 24. However, the input device 24 may be a keyboard, a touch panel, a touch pad, a trackball, a joystick, and the like.

The above-mentioned medical image processing method is configured as a program that causes a computer to implement each step, and a non-transitory recording medium, such as a compact disk-read only memory (CD-ROM), in which this program is stored can also be configured.

The processor 14 includes, for example, a central processing unit (CPU) which is a general-purpose processor executing software (programs) to function as various processing units, a graphics processing unit (GPU) which is a processor specializing in image processing, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or by two or more processors of the same type or different types (for example, a combination of a plurality of FPGAs, a combination of a CPU and an FPGA, or a combination of a CPU and a GPU). Further, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). As described above, various processing units are configured using one or more of the various processors as a hardware structure.

In addition, specifically, an electric circuit (circuitry) obtained by combining circuit elements, such as semiconductor elements, is used as the hardware structure of the various processors.

The technical scope of the invention is not limited to the scope according to the above-described embodiment. The configurations and the like in the embodiment can be appropriately combined without departing from the gist of the invention.

EXPLANATION OF REFERENCES

10: medical image display system
12: medical image processing device
14: processor 16: memory
18: medical image storage device
20: medical image viewer device
22: display
24: input device
26: in-hospital network
28: CT device
30: MM device
S1 to S12: step of process of method for storing extracted region data of anatomical feature structure
S21 to S32: step of process of medical image display method

What is claimed is:

1. A medical image processing device comprising:
a memory that stores commands to be executed by a processor; and
the processor that executes the commands stored in the memory,
wherein the processor
outputs a signal for displaying a first medical image of a subject,
acquires a position, which is designated by a user, in the first medical image,
identifies an anatomical feature structure closest to the designated position in the first medical image,
acquires a second medical image of the subject that was captured in the past and that includes the identified anatomical feature structure,
registers the first medical image with the second medical image,
cuts out a region of interest including the identified anatomical feature structure from the second medical image based on a registration result to generate a second partial region image, and
outputs a signal for displaying the second partial region image to be superimposed on the first medical image,
wherein the region of interest has, as a center, a position that is anatomically the same as the designated position in the first medical image.

2. The medical image processing device according to claim 1,
wherein the processor estimates a position of the identified anatomical feature structure in the second medical image and registers the first medical image with the second medical image, using a position of the identified anatomical feature structure in the first medical image and the estimated position of the anatomical feature structure in the second medical image.

3. The medical image processing device according to claim 1,
wherein the processor cuts out a region including the identified anatomical feature structure from the first medical image to generate a first partial region image and outputs a signal for displaying the first partial region image side by side with the second partial region image.

4. The medical image processing device according to claim 3,
wherein the first partial region image and the second partial region image are images with the same size.

5. The medical image processing device according to claim 1,
wherein the processor outputs a signal for displaying a frame, which surrounds a region including the identified anatomical feature structure of the first medical image, to be superimposed on the first medical image.

6. The medical image processing device according to claim 5,
wherein the processor outputs a signal for displaying the second partial region image at a position where the second partial region image does not overlap the frame.

7. The medical image processing device according to claim 1,
wherein the processor outputs a signal for displaying a difference image indicating a difference between the first medical image and the second medical image to be superimposed on the first medical image.

8. The medical image processing device according to claim 1,
wherein the processor adjusts a quality of the first medical image under a first image quality adjustment condition and adjusts a quality of the second medical image under the first image quality adjustment condition.

9. The medical image processing device according to claim 8,
wherein the quality of the first medical image and the quality of the second medical image are adjusted using a sharpness process for edge enhancement.

10. The medical image processing device according to claim 1,
wherein the anatomical feature structure includes at least one of an organ, a bone, a muscle, or a lesion region.

11. The medical image processing device according to claim 1,
wherein the first medical image and the second medical image include an image captured by any of a computed tomography (CT) device, a magnetic resonance imaging (MRI) device, a positron emission tomography (PET) device, an ultrasound diagnostic device, or a computed radiography (CR) device.

12. The medical image processing device according to claim 1,
wherein the processor outputs a signal for displaying a part of the second partial region image so as to be superimposed on the first medical image.

13. The medical image processing device according to claim 1,
wherein the processor outputs a signal for displaying the second partial region image at a position where the second partial region image does not cover a region which is anatomically the same as the second partial region image, in the first medical image.

14. The medical image processing device according to claim 1,
wherein the processor cuts out a rectangular region including the identified anatomical feature structure from the second medical image, to generate the second partial region image.

15. A medical image display system comprising:
the medical image processing device according to claim 1;
a display that displays an image based on an acquired signal; and
an input device that designates a position in the image displayed on the display.

16. A medical image processing method comprising:
a first medical image display step of outputting a signal for displaying a first medical image of a subject;
a designated position acquisition step of acquiring a position, which is designated by a user, in the first medical image;

an anatomical feature structure identification step of identifying an anatomical feature structure closest to the designated position in the first medical image;

a second medical image acquisition step of acquiring a second medical image of the subject that was captured in the past and that includes the identified anatomical feature structure;

a registration step of registering the first medical image with the second medical image;

a second medical image cutout step of cutting out a region of interest including the identified anatomical feature structure from the second medical image based on a registration result to generate a second partial region image; and a second medical image display step of outputting a signal for displaying the second partial region image to be superimposed on the first medical image, wherein the region of interest has, as a center, a position that is anatomically the same as the designated position in the first medical image.

17. A non-transitory, computer-readable tangible recording medium on which a program for causing, when read by a computer, the computer to execute the medical image processing method according to claim 16 is recorded.

* * * * *